(12) United States Patent
Omori

(10) Patent No.: US 7,959,471 B2
(45) Date of Patent: Jun. 14, 2011

(54) ELECTRICAL CONNECTOR

(75) Inventor: Koji Omori, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 99 days.

(21) Appl. No.: 12/361,016

(22) Filed: Jan. 28, 2009

(65) Prior Publication Data

US 2009/0215322 A1    Aug. 27, 2009

(30) Foreign Application Priority Data

Feb. 27, 2008    (JP) .................. 2008-046649

(51) Int. Cl.
   *H01R 24/00*    (2006.01)
(52) U.S. Cl. ....................................................... 439/630
(58) Field of Classification Search .................. 439/228, 439/218, 630, 639, 638, 660, 668, 540.1
See application file for complete search history.

(56) References Cited

U.S. PATENT DOCUMENTS 7,131,860 B2 *   11/2006   Sartor et al. .................. 439/489
2007/0134987 A1 *   6/2007   Yen ................................ 439/630

FOREIGN PATENT DOCUMENTS

JP    2002-190352    7/2002

* cited by examiner

*Primary Examiner* — Alexander Gilman
(74) *Attorney, Agent, or Firm* — Scully, Scott, Murphy & Presser, P.C.

(57) ABSTRACT

A first groove portion into which a first plug connector can fit and a second groove portion that surrounds the first groove portion and into which a second plug connector can fit are formed in a receptacle connector. By arranging first receiving-side contacts that contact against and conduct with contacts of the first plug connector in the first groove portion and arranging second receiving-side contacts that contact against and conduct with contacts of the second plug connector in the second groove portion, plug connectors with mutually different shapes and in which the number of contacts are mutually different can be easily and reliably connected to a common receptacle connector. It is therefore possible to reduce the mounting space of the receptacle connector to prevent an increase in the apparatus size, and also improve the usability.

8 Claims, 21 Drawing Sheets

ELECTRICAL CONNECTOR

This application claims benefit of Japanese Application No. 2008-046649 filed in Japan on Feb. 27, 2008; the contents of which are incorporated by this reference.

BACKGROUND OF THE INVENTION

1. Field of the Invention

The present invention relates to an electrical connector that includes a receptacle connector and a plug connector that is fitted in the receptacle connector.

2. Description of the Related Art

Conventionally, when connecting one device with another device to send and receive signals, a male plug connector is provided via a cable or the like in the device on the side sending the signals, and by fitting the plug connector to a female receptacle connector provided on the receiving side, the devices are electrically connected to each other. With electrical connectors that include this kind of receptacle connector and plug connector, there is a need for the connection (fitting) of the connectors to be performed easily and surely, and for the connection reliability (contact reliability of contacts) to be ensured under the usage environment.

For example, Japanese Patent Application Laid-Open Publication No. 2002-190352 discloses prior art relating to an electrical connector including a receptacle connector and a plug connector that is fitted to the receptacle connector. That prior art describes technology that aims to simplify the locking mechanism of the connector and also facilitate removal of fluid that adheres to the connector.

In this connection, it is not always necessary to maintain a one-to-one relation between a device on a side sending a signal and a device on a side receiving the signal, and conventionally devices have been designed to provide upward compatibility to enable common use of the device on the signal-receiving side, i.e. the device on the signal processing side, with respect to a plurality of devices on the signal-sending side.

For example, endoscopes of various kinds are used in the field of medical treatment, and by connecting a plug connector provided in an endoscope to a receptacle connector of a signal processing apparatus it is possible to display picked-up images of affected areas or perform medical treatment using a treatment instrument and the like. With such kinds of endoscopes, there are cases in which, even though the endoscopes are of the same kind, a mixture of conventional endoscopes and endoscopes that have been newly developed in conformity with technological progress are utilized. Therefore designing a processing apparatus that is compatible with a new-model endoscope in a manner such that the processing apparatus can also be applied to a conventional endoscope is also beneficial from the viewpoints of effective utilization of the product and cost reductions.

SUMMARY OF THE INVENTION

According to one aspect of the present invention, there is provided an electrical connector that includes: a first plug connector having a first protruding portion on which first contacts are arranged; a second plug connector having a pair of second protruding portions on which second contacts are respectively arranged; and a receptacle connector that has an opening into which the first plug connector and the second plug connector can be selectively inserted, a first groove portion that is provided inside the opening and into which the first protruding portion of the first plug connector can fit, first receiving-side contacts that are arranged inside the first groove portion so as to electrically conduct with the first contacts in a state in which the first protruding portion has been fitted therein, a pair of second groove portions that are provided so as to surround the first groove portion, and into which the pair of second protruding portions can fit, and second receiving-side contacts that are arranged inside the pair of second groove portions, respectively, so as to electrically conduct with the second contacts in a state in which the pair of second protruding portions have been fitted therein.

According to another aspect of the present invention, there is provided an electrical connector that includes: a first plug connector having a first protruding portion on which first contacts are arranged; a second plug connector having a pair of second protruding portions on which second contacts are respectively arranged, and which are spaced at an interval that is greater than a thickness of the first protruding portion; and a receptacle connector that is capable of selectively connecting the first plug connector and the second plug connector.

According to a further aspect of the present invention, there is provided an electrical connector that includes: a first plug connector having a first protruding portion on which first contacts are arranged; a second plug connector having a pair of second protruding portions on which second contacts are respectively arranged, and in which the pair of second protruding portions are spaced at an interval that is greater than a thickness of the first protruding portion of the first plug connector; and a receptacle connector in which first receiving-side contacts capable of electrically conducting with the first contacts of the first plug connector are arranged inside a first groove portion into which the first protruding portion of the first plug connector can fit, and in which second receiving-side contacts capable of electrically conducting with the second contacts of the second plug connector are arranged inside a pair of second groove portions into which the pair of second protruding portions of the second plug connector that are provided so as to surround the first groove portion can fit.

DETAILED DESCRIPTION OF THE PREFERRED EMBODIMENTS

An embodiment of the present invention is described hereunder with reference to the drawings.

Figure 1:
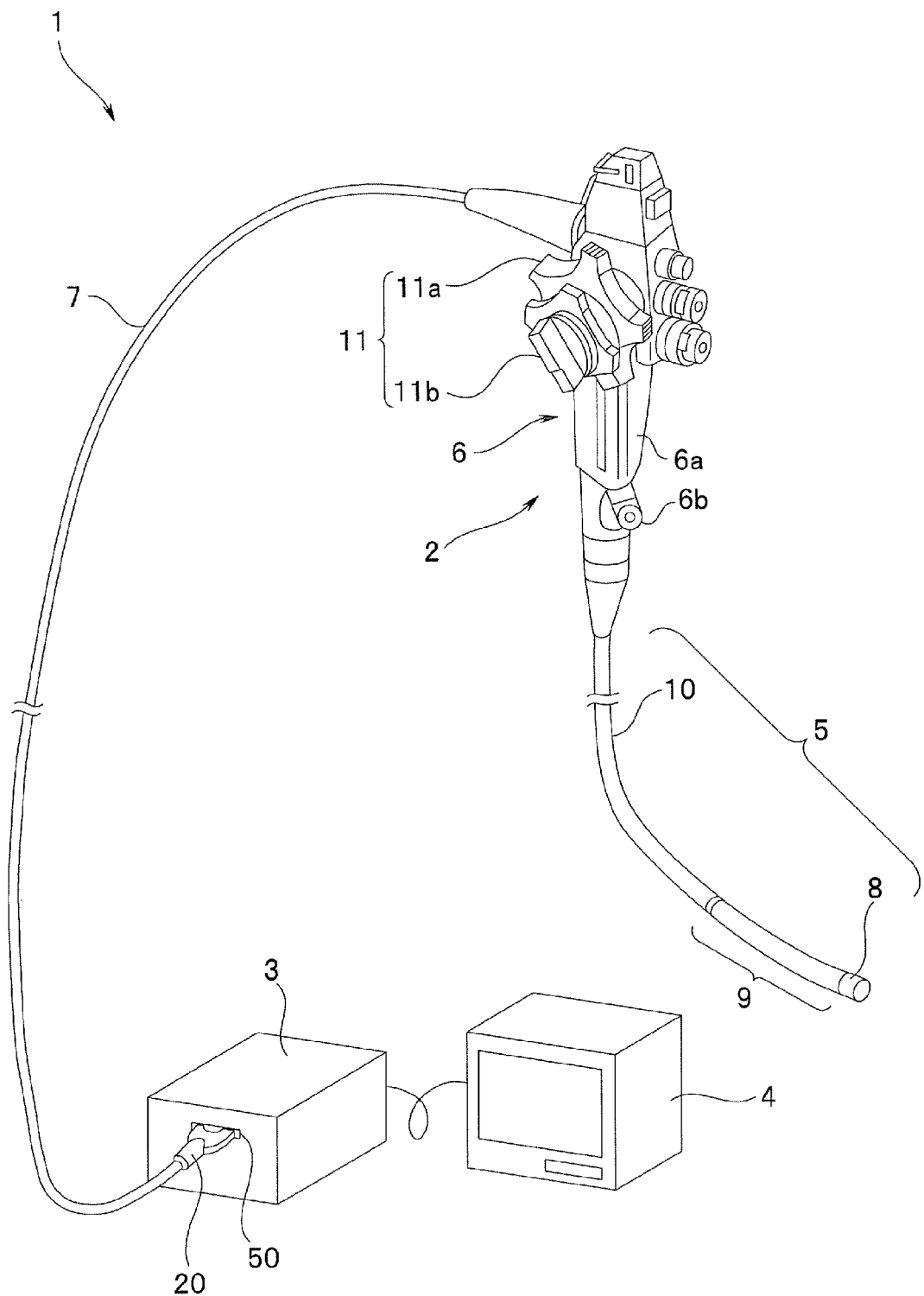
FIG. 1 is an overall configuration diagram of an endoscope apparatus to which the present invention is applied.

In FIG. 1, reference numeral 1 denotes an endoscope apparatus that illustrates one example of application of the electrical connector according to the present invention. The endoscope apparatus 1 has an endoscope 2, a processing device (hereunder, referred to as "video processor") 3 that is connected to the endoscope 2 to supply an illumination light thereto and perform various kinds of signal processing, and a monitor 4 that receives signals that are output from the video processor 3 to display images of an observation site and the like.

The endoscope 2 has an insertion portion 5 that is an elongated, hollow-shaped long member that is inserted to a site that is an object of observation, an operation portion 6 that has a grasping portion 6a that is connected to a proximal end portion of the insertion portion 5, and a universal cable 7 that extends from a side surface of the operation portion 6. The insertion portion 5 has a distal-end portion 8 that has an illumination system and an imaging system and the like contained therein on the distal-end side. A bending portion 9 as a portion that is bendable and movable is linked to the rear portion of the distal-end portion 8.

A flexible tube portion 10 that is long and flexible and formed of a flexible tube-shaped member is connected to the rear of the bending portion 9. Further, a bending operation portion 11 that has a bending operation knob 11a for performing bending operations of the bending portion 9 and a fixing lever 11b for fixing the bending operation knob 11a at a desired rotational position and the like are provided in a prescribed manner on the operation portion 6.

In this connection, reference numeral 6b denotes a treatment instrument insertion opening that communicates with the proximal end of a treatment instrument channel (not shown) that is passed through the insertion portion 5.

The endoscope 2 and the video processor 3 are electrically connected by an electrical connector that includes a plug connector 20 provided at an end of the universal cable 7 of the endoscope 2 and a receptacle connector 50 provided in the video processor 3. According to the present embodiment, the plug connector 20 and the receptacle connector 50 are flat connectors, and it is possible to electrically connect the plug connector 20 and the receptacle connector 50 by detachably fitting the plug connector 20 in the receptacle connector 50 to cause the contacts of each connector to contact mechanically.

Figure 2A:
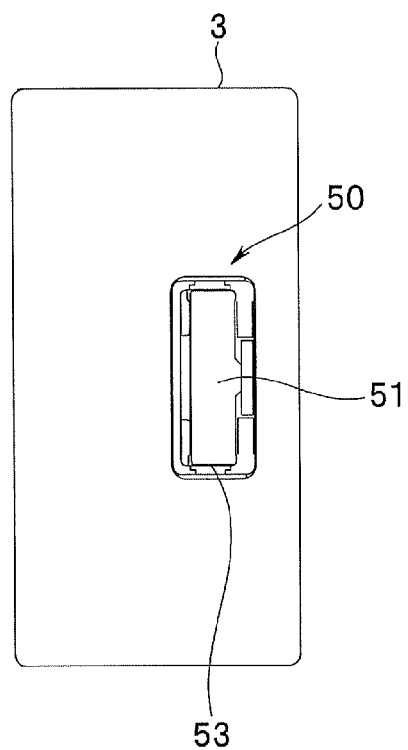
FIG. 2A is a view as seen from a front side of a receptacle connector that is provided in a video processor.
Figure 2B:
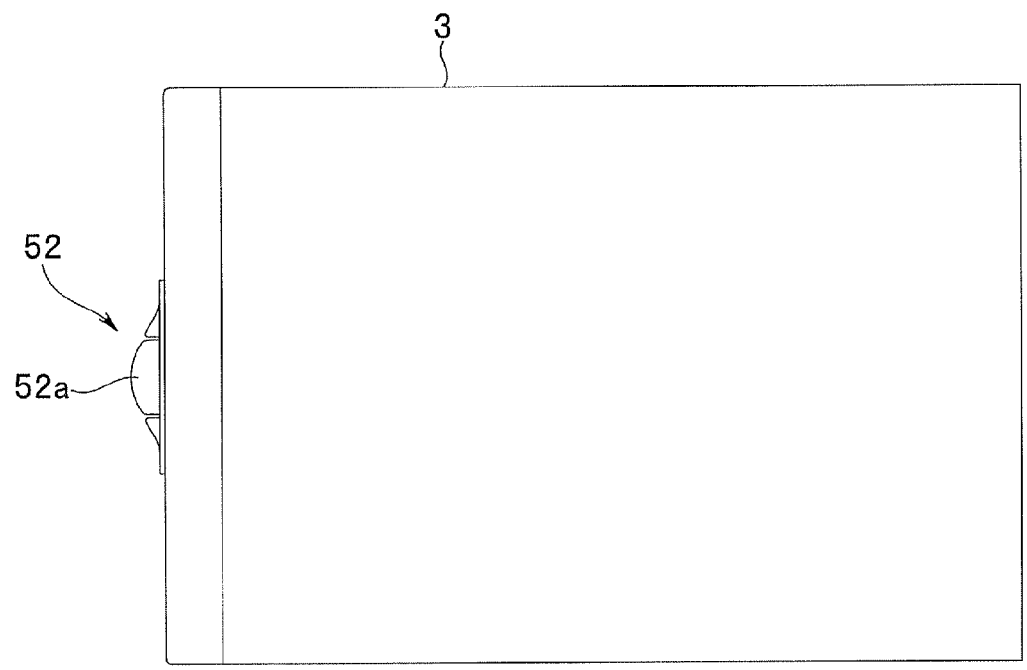
FIG. 2B is a view as seen from a side surface side of the receptacle connector that is provided in the video processor.

As shown in FIG. 2A and FIG. 2B, the receptacle connector 50 is arranged so that an opening 51 for inserting and fitting the plug connector 20 is exposed on one side of the case of the video processor 3. A locking mechanism portion 52 for retaining the plug connector 20 in a fitted state or releasing the plug connector 20 is provided in the receptacle connector 50. A tabular lid member 53 is arranged at a position that is slightly recessed from the front face of the opening 51. The locking mechanism portion 52 is set by inserting and fitting the plug connector 20 into the receptacle connector 50, and is released by pushing in a lever 52a.

FIG. 2A is a view showing the opening 51 of the receptacle connector 50 provided in the casing of the video processor 3 when the receptacle 50 is viewed from the front side. FIG. 2B is a view showing the lever 52a of the locking mechanism portion 52 of the receptacle connector 50 when viewed from the side surface side of the casing of the video processor 3.

The lid member 53 provided in the receptacle connector 50 fulfills a function of blocking the opening 51 to prevent entry of foreign matter when the receptacle connector 50 is not in use (when the plug connector 20 is not inserted into the receptacle connector 50), and also acts as a preliminary-stage portion of a wiper mechanism for preventing electrolytic corrosion of metal members that form the contacts. The wiper mechanism is provided in order to deal with cases in which a fluid such as water or a chemical remains on a contact portion of the plug connector 20 due to washing or sterilization or the like of the endoscope 2, and is configured to wipe off residual fluid (hereunder, the residual fluid is described as moisture as a representative thereof) on the contact portion in two stages when the plug connector 20 is inserted into the opening 51. The wiper mechanism is described later.

Figure 3:
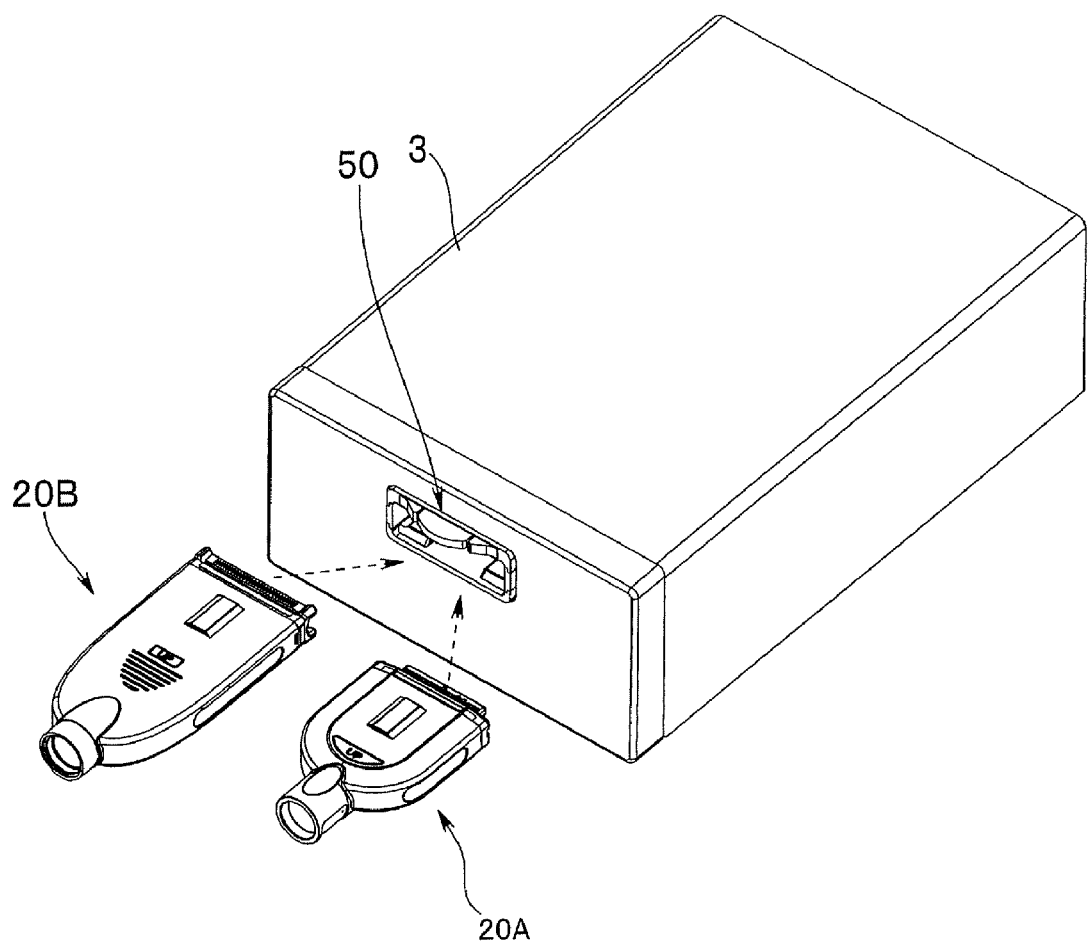
FIG. 3 is an oblique perspective view that illustrates two kinds of plug connectors that are to be connected to the receptacle connector of the video processor.
Figure 4:
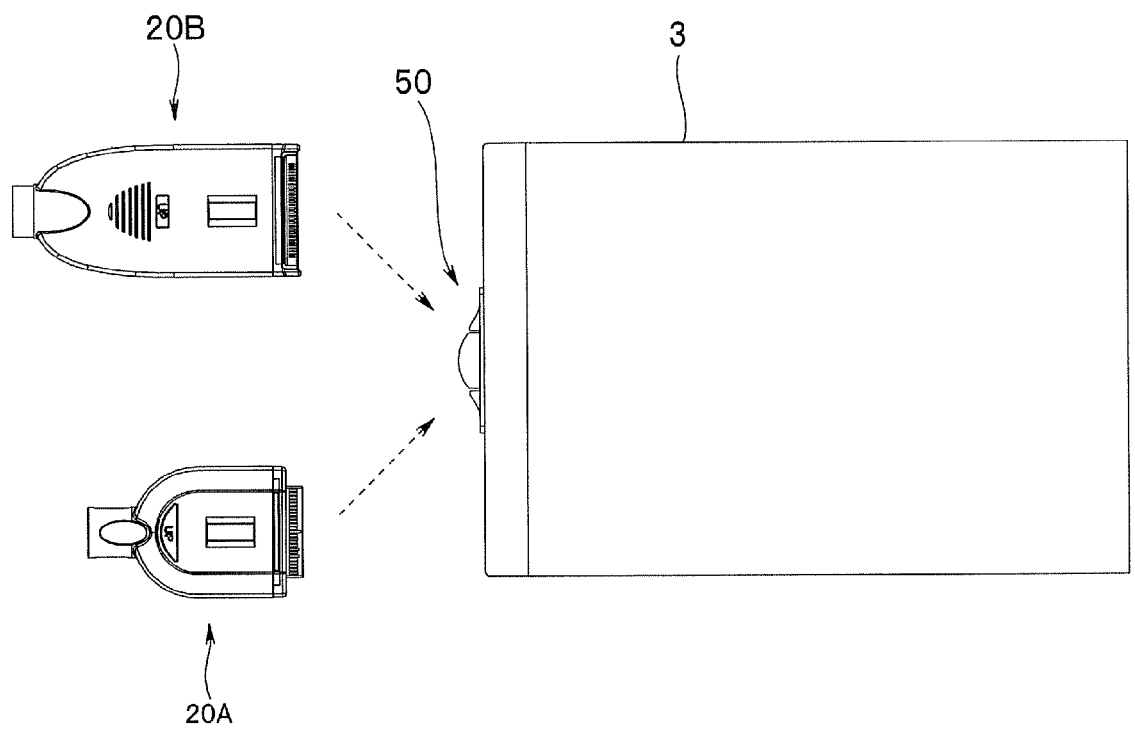
FIG. 4 is a plan view that illustrates the two kinds of plug connectors to be connected to the receptacle connector of the video processor.
Figure 5:
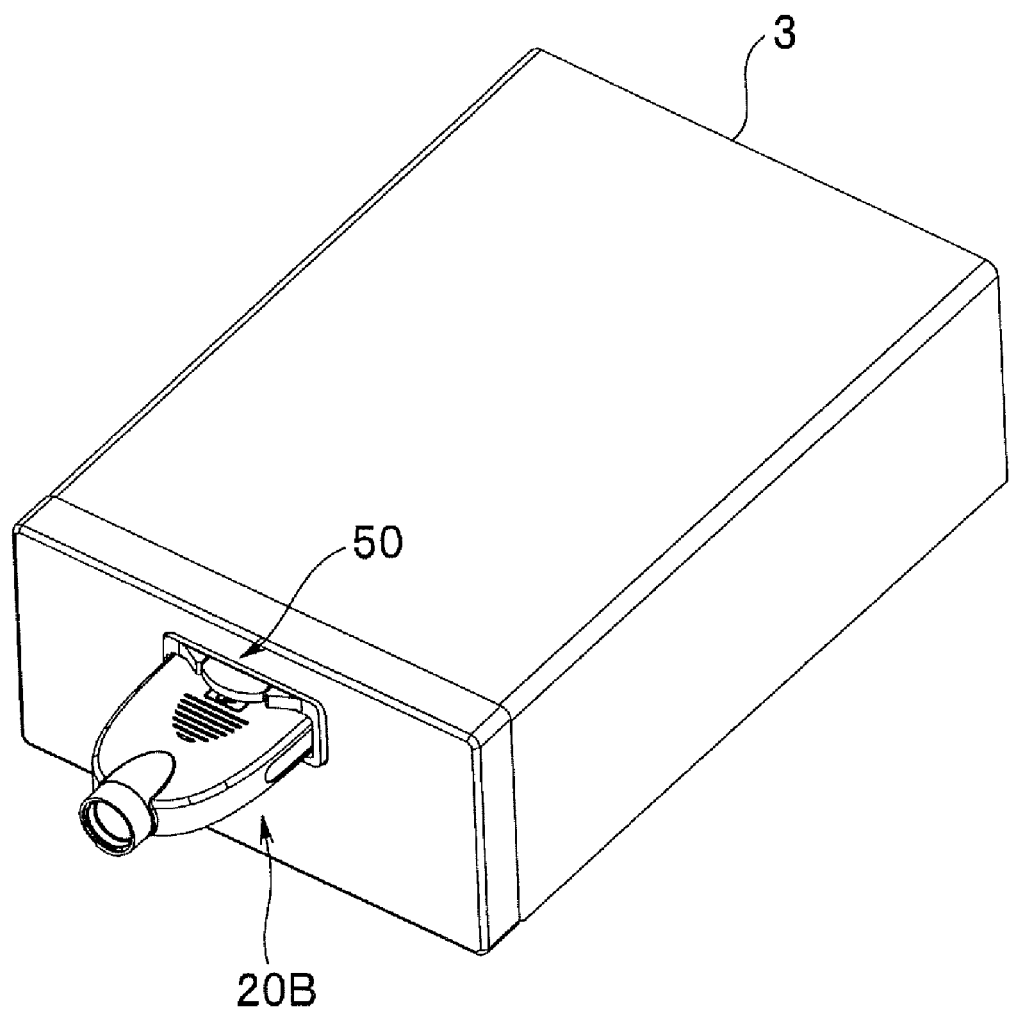
FIG. 5 is an oblique perspective view showing a state in which a plug connector is connected to the receptacle connector of the video processor.

Further, as shown in FIG. 3 and FIG. 4, the receptacle connector 50 is configured as a connector with a multiple receptacle structure that can selectively connect first and second plug connectors 20A and 20B as the plug connector 20. The first and second plug connectors 20A and 20B are respectively connected to the ends of cables that extend from a first and a second device that are different to each other. The first and second plug connectors 20A and 20B are connectors in which the number of contacts, the arrangement of contacts and the like are mutually different.

In the present embodiment, the first and second devices to which the first and second plug connectors 20A and 20B are connected are two kinds of mutually different endoscopes, and although the models and time of product commercialization and the like are different, the first and second devices are devices in which signal processing can be performed with the same video processor 3. For example, the endoscope 2 is a new model endoscope that has been newly brought to the market, and the second plug connector 20B is provided in the new model endoscope 2. In a case in which the first plug connector 20A is a connector provided in an endoscope (not shown) for which the model or time of commercialization is prior to the endoscope 2, the second plug connector 20B is formed as a connector that, accompanying an increase in the number of signals to be processed, has a greater number of contacts than the first plug connector 20A. The video processor 3 is equipped with a function capable of processing the input/output signals of these two kinds of endoscopes.

According to the present embodiment, the second plug connector 20B is slightly wider than the first plug connector 20A, and the size in the thickness direction of the plug connectors 20A and 20B including a protrusion portion is substantially the same. Therefore, as shown in FIG. 5 and FIG. 6A to FIG. 6C, the width in the lateral direction of the opening 51 of the receptacle connector 50 is designed to match the width of the second plug connector 20B, and the size in the vertical direction of the opening 51 is designed to match the thickness of both the plug connectors 20A and 20B. However, the configuration is not necessarily limited thereto, and the first plug connector 20A and the second plug connector 20B may be the same width.

Figure 6A:
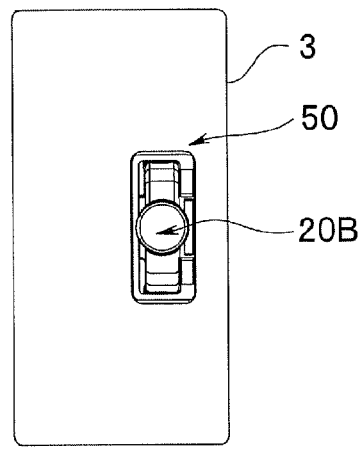
FIG. 6A is a view showing a state in which the plug connector is connected to the receptacle connector of the video processor as viewed from the front direction.
Figure 6B:
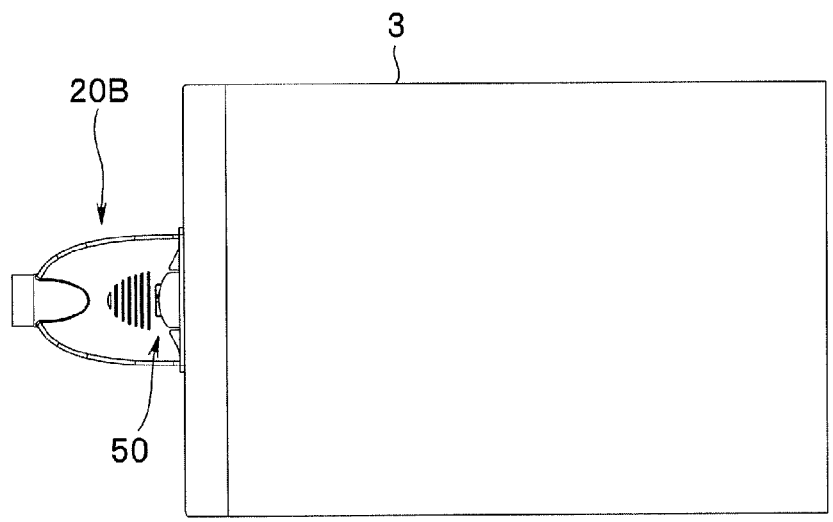
FIG. 6B is a view showing a state in which the plug connector is connected to the receptacle connector of the video processor as viewed from a side direction.
Figure 6C:
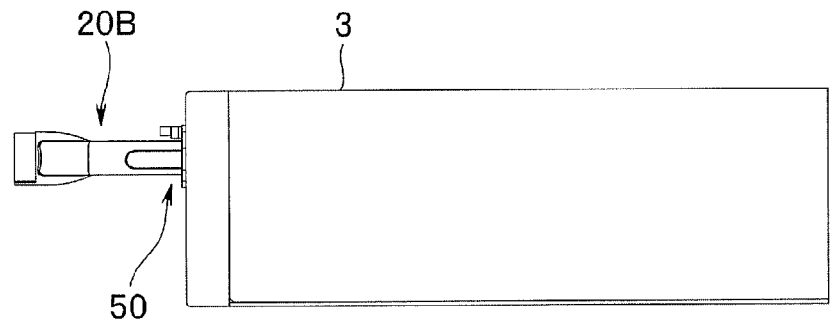
FIG. 6C is a view showing a state in which the plug connector is connected to the receptacle connector of the video processor as viewed from the underside direction.
Figure 7:
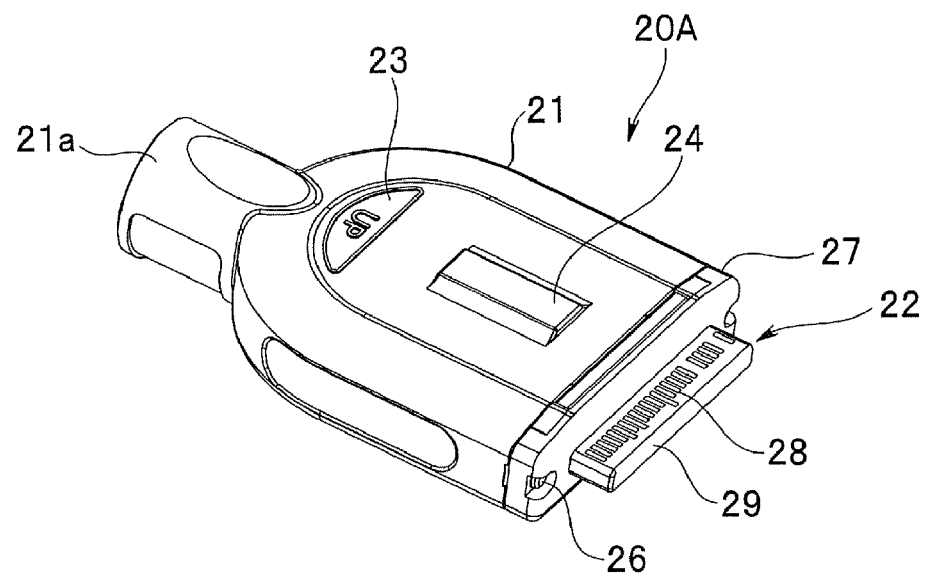
FIG. 7 is an oblique perspective view showing the outer appearance of a first plug connector.

Regarding FIG. 6A to FIG. 6C, FIG. 6A shows the shape of the plug connector 20B inserted into the receptacle 50 of the video processor 3 as viewed from the front surface direction (cable side), FIG. 6B shows the shape of the plug connector 20B as viewed from the side direction of the video processor 3 (locking mechanism portion 52 side of the receptacle 50), and FIG. 6C shows the shape of the plug connector 20B as viewed from the underside direction of the video processor 3.

[Configuration of Plug Connectors]

The first and second plug connectors 20A and 20B have the external shapes and contact configurations illustrated in FIG. 7 to FIG. 13 in detail. In the present embodiment, the first plug connector 20A and the second plug connector 20B are formed as flat connectors that have substantially the same shape in terms of their outer appearance except for the number and arrangement of contacts. This is because, when taking into account the usability of the connectors, it is desirable not to significantly change the outer shape of the connectors. However, the present invention is not limited thereto, and can also be applied to a case in which the outer shapes of two kinds of connectors are different.

(First Plug Connector)

First, the first plug connector 20A is described. As shown in FIG. 7 and FIG. 8A to FIG. 8D, the first plug connector 20A includes a flat exterior case 21 that integrally includes a cylindrical sleeve 21a into which a cable (not shown) is inserted, and a terminal retaining portion 22 that protrudes from the front end of the exterior case 21. Of the exterior case 21 and the terminal retaining portion 22, at least the terminal retaining portion 22 is formed of an insulating member such as a resin material.

On one surface side of the two flat outer surfaces of the exterior case 21, an "UP" mark 23 is formed at a region on the sleeve 21a side. The "UP" mark 23 is used for confirming the orientation when inserting the first plug connector 20A into the receptacle connector 50. To the front of the "UP" mark 23 is provided an elongated protrusion portion 24 that engages with the locking mechanism portion 52 of the receptacle connector 50.

Figure 9:
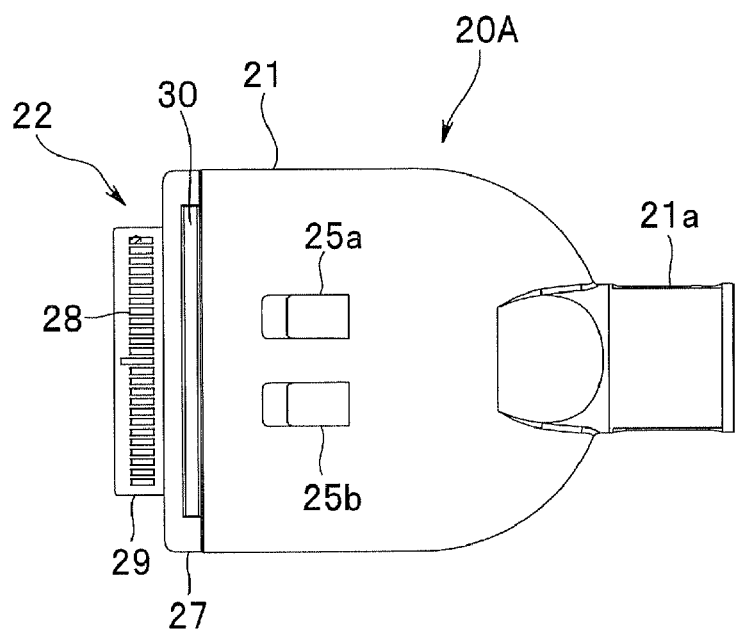
FIG. 9 is a bottom view of the first plug connector.
Figure 8A:
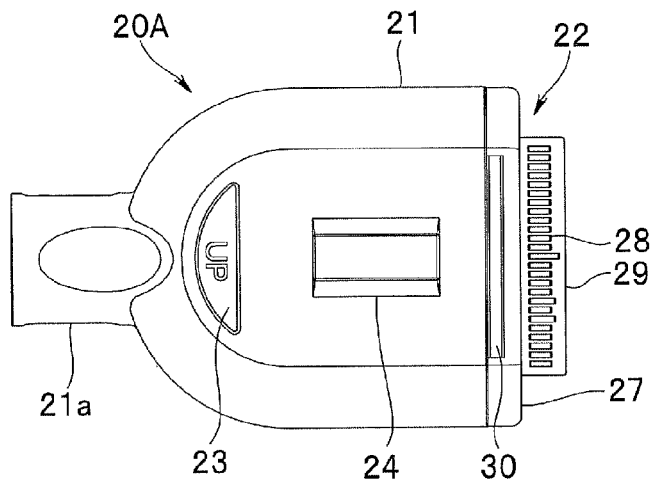
FIG. 8A is a front view of the first plug connector.
Figure 8B:
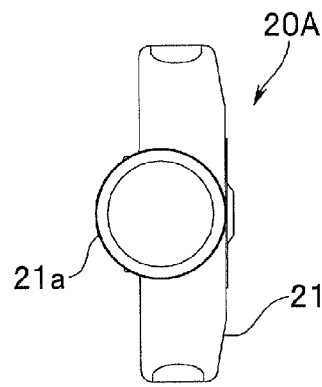
FIG. 8B is a left side view of the first plug connector.
Figure 8C:
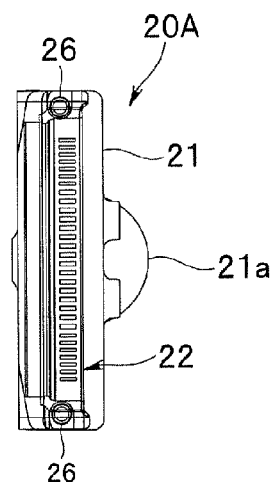
FIG. 8C is a right side view of the first plug connector.
Figure 8D:
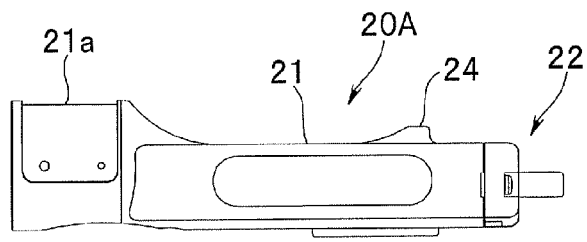
FIG. 8D is a top view of the first plug connector.
Figure 10:
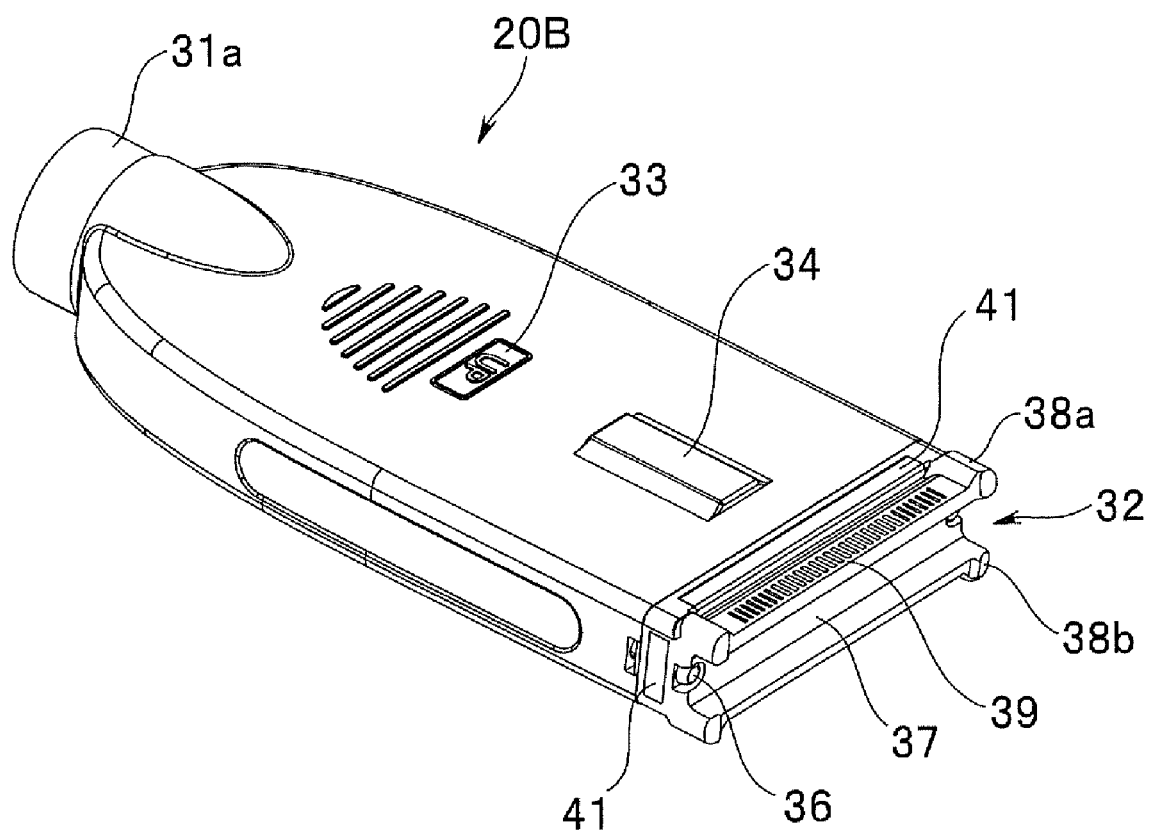
FIG. 10 is an oblique perspective view showing the outer appearance of a second plug connector.
Figure 14:
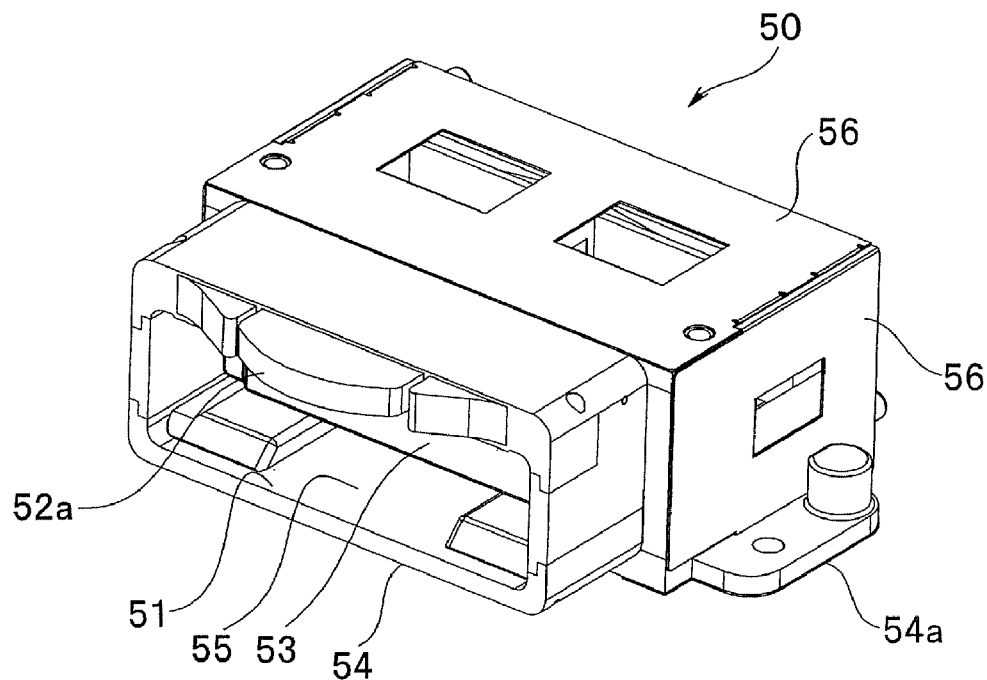
FIG. 14 is an oblique perspective view showing the outer appearance of a receptacle connector.

Regarding FIG. 8A to FIG. 8D, FIG. 8A is a view that shows the surface on which the "UP" mark 23 is formed as the front, FIG. 8B is a left side view, FIG. 8C is a right side view, and FIG. 8D is a top view. Further, as shown in FIG. 9, on the bottom surface on the side opposite to the surface on which the "UP" mark 23 is formed, elongated protrusion portions 25a and 25b are formed that engages with a groove portion 55 (see FIG. 14) provided in a lower inner wall of the receptacle connector 50.

The terminal retaining portion 22 includes a flange portion 27 that is fixed via screws 26 to the front face of the exterior case 21, and a protruding portion 29 that protrudes from the flange portion 27 and in which a plurality of elongated electrical contacts 28, 28 . . . are provided. The plurality of elongated electrical contacts 28, 28 . . . are integrally embedded in the terminal retaining portion 22, and are arranged so as to be exposed at predetermined intervals on the top and bottom surfaces of the protruding portion 29. Each of the electrical contacts 28, 28 . . . is arranged so that a terminal thereof is extended into the exterior case 21 to be exposed therein from the proximal side of the protruding portion 29 so as to connect to a corresponding cable wire directly or via a substrate or the like inside the exterior case 21, and one portion of the terminals is connected to a grounding conductive member 30 that is provided on the top and bottom surfaces of the flange portion 27.

(Second Plug Connector)

As shown in FIG. 10 and FIG. 11A to FIG. 11D, the second plug connector 20B includes a flat exterior case 31 that integrally includes a cylindrical sleeve 31a into which a cable is inserted, and a terminal retaining portion 32 that protrudes from the front end of the exterior case 31. Of the exterior case 31 and the terminal retaining portion 32, at least the terminal retaining portion 32 is formed of an insulating member such as a resin material.

The exterior case 31 is formed to have a wider width than the exterior case 21 of the first plug connector 20A, and on one surface side of the two flat outer surfaces thereof, an "UP" mark 33 is formed at a region on the sleeve 31a side. The "UP" mark 33 is used for confirming the orientation when inserting the second plug connector 20B into the receptacle connector 50. To the front of the "UP" mark 33 is provided an elongated protrusion portion 34 that engages with the locking mechanism portion 52 of the receptacle connector 50.

Figure 11A:
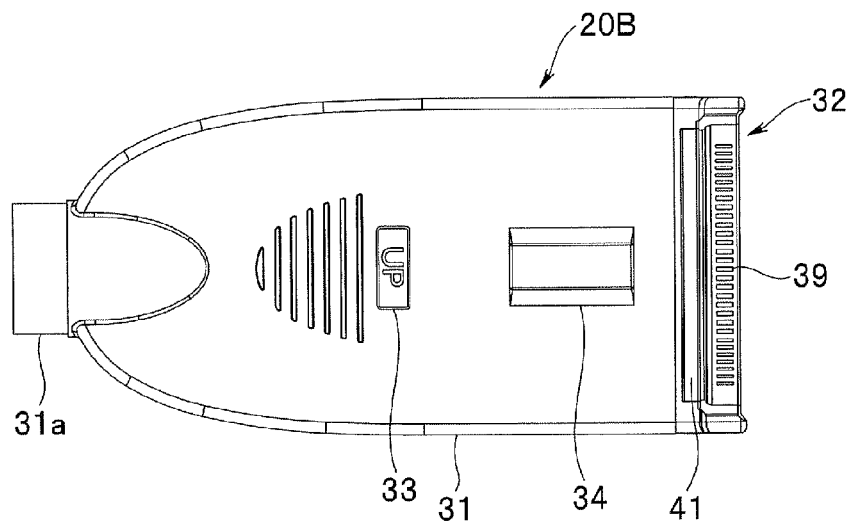
FIG. 11A is a front view of the second plug connector.
Figure 11B:
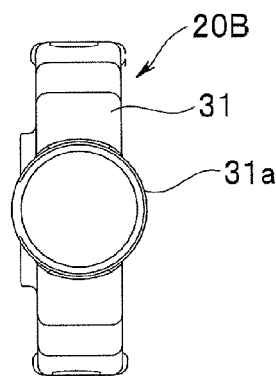
FIG. 11B is a left side view of the second plug connector.
Figure 11C:
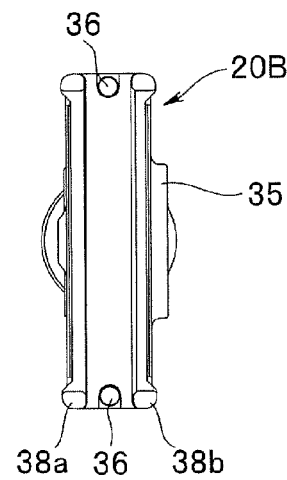
FIG. 11C is a right side view of the second plug connector.
Figure 11D:
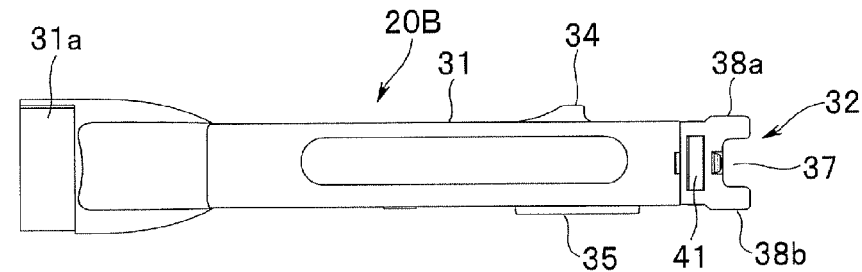
FIG. 11D is a top view of the second plug connector.

Regarding FIG. 11A to FIG. 11D, FIG. 11A is a view that shows the surface on which the "UP" mark 33 is formed as the front, FIG. 11B is a left side view, FIG. 11C is a right side view, and FIG. 11D is a top view. Further, on the bottom surface on the side opposite to the surface on which the "UP" mark 33 is formed, an elongated protrusion portions 35 is formed that engages with a groove portion 55 (see FIG. 14) provided in a lower inner wall of the receptacle connector 50.

In this connection, although according to the present embodiment the protrusion portions 25a and 25b of the first plug connector 20A that fit in the groove portion 55 of the receptacle 50 and the protrusion portion 35 of the second plug connector 20B that fits in the groove portion 55 of the receptacle 50 are different shapes, the fitting widths of the protrusion portions with respect to the groove portion 55 of the receptacle 50 may be the same width and the protrusion portions may be the same shape.

The terminal retaining portion 32 is fixed through screws 36 to the front of the exterior case 31, and a pair of protruding portions 38a and 38b protrude via a concave portion 37 to the front end side. Each of the protruding portions 38a and 38b is formed substantially parallel to the surface on the protrusion portion 35 side that is on the opposite side to the surface on the "UP" mark 33 side, and a plurality of electrical contacts 39, 39 . . . are disposed at predetermined intervals on the respective surfaces of the protruding portions 38a and 38b.

The electrical contacts 39, 39 . . . are integrally embedded in the terminal retaining portion 32, and are arranged so that a plurality of terminals extend into the exterior case 31 to be exposed therein from the proximal side of the protruding portions 38a and 38b so as to connect with a corresponding signal wire directly or via a substrate or the like inside the exterior case 31, and one portion of the terminals is connected to a grounding conductive member 41 that is provided on the proximal side of the terminal retaining portion 32. The grounding conductive member 41 is provided at four locations including the top and bottom surfaces and the left and right sides of the proximal portion of the terminal retaining portion 32 in correspondence to an increase in signal lines to thereby enhance the grounding performance.

The pair of protruding portions 38a and 38b has a groove-shape hollow that can accommodate the protruding portion 29 of the first plug connector 20A, and are designed to sandwich the protruding portion 29. More specifically, when the electrical contacts 28, 28 . . . of the first plug connector 20A are taken as first contacts, the protruding portion 29 in which the first contacts are provided is taken as a first protruding portion, the electrical contacts 39, 39 . . . of the second plug connector 20B are taken as second contacts, and the pair of protruding portions 38a and 38b in which the second contacts are arranged are taken as second protruding portions, the configuration is such that the pair of second protruding portions are spaced apart larger than the thickness of the first protruding portion and, as described later, two kinds of receiving-side contacts that contact the first and second contacts can be disposed with the minimal space inside the single receptacle connector 50.

Figure 12:
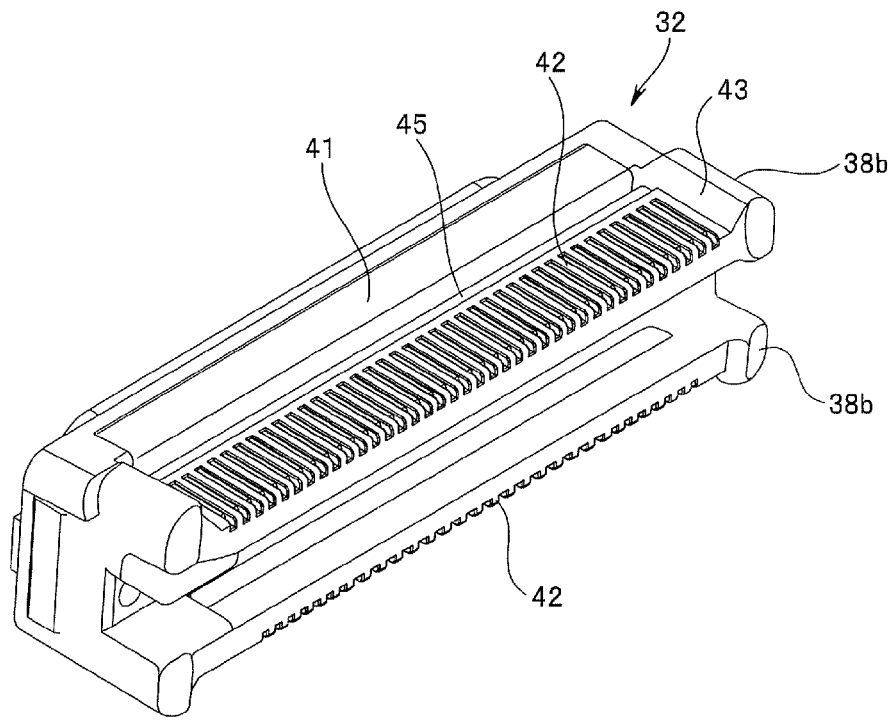
FIG. 12 is an oblique perspective view that illustrates a terminal retaining portion of the second plug connector.
Figure 13:
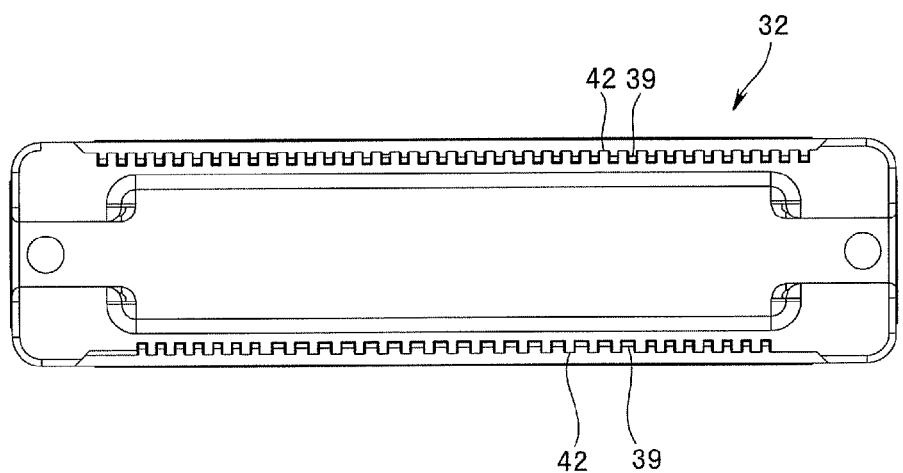
FIG. 13 is an explanatory drawing illustrating contact surfaces of the terminal retaining portion of the second plug connector.

As shown in FIG. 12 and FIG. 13, regarding the protruding portions 38a and 38b that protrude from the terminal retaining portion 32, the regions on both sides in the width direction are formed so as to protrude with a slight difference in level from the surfaces on which conductive members 41 are provided on the proximal side, and at positions that are lower than the proximal side and that have a predetermined difference in level from the two side regions, contact disposition surfaces 42 on which electrical contacts 39, 39 . . . are disposed are respectively formed. That is, the respective contact disposition surfaces 42 of the protruding portions 38a and 38b are formed so that both sides thereof are enclosed by a bank-shaped step portion 43. In this connection, the bank-shaped step portion 43 also protrudes slightly to the front with respect to the contact disposition surfaces 42.

Further, the electrical contacts 39, 39 . . . are provided in an embedded condition so that the contact surfaces are exposed at a slightly lower position with respect to the contact disposition surfaces 42, and have a contact structure in which the respective contacts are disposed via a wall. Further, groove-shaped concave portions 45 are respectively provided between the regions in which the conductive members 41 on the proximal side of the terminal retaining portion 32 are disposed and the contact disposition surfaces 42.

Thus, when wiping off in two stages moisture that attaches to the contact disposition surfaces 42 using a wiper mechanism of the receptacle connector 50 that is described later, it is possible to prevent moisture that was been wiped from moving to another region by allowing moisture that flows out laterally from one of the contact disposition surfaces 42 to flow around to the contact disposition surfaces 42 on the opposite side in the initial wiping stage. Further, when wiping off a slight amount of moisture that remains on the contact disposition surface 42 at the next stage, it is possible to accumulate the small amount of wiped moisture inside the groove-shaped concave portions 45 that are formed towards the rear in the insertion direction of the contact disposition surface 42 to thereby keep the moisture away from the vicinity of the contact portion, and thus prevent moisture adhering to another conductive region so that the occurrence of electrolytic corrosion can be prevented.

Further, by disposing the contact surfaces of electrical contacts 39, 39 . . . at a recessed position in which respective contacts are separated via walls as a position that is lower than the contact disposition surfaces 42 enclosed by the bank-shaped step portions 43, it is possible to prevent conduction by a bridge between contacts and protect contact surfaces from physical external force such as in a case in which the plug connector is dropped or is knocked against another region, and thereby avoid mechanical damage such as scratching on the contact surfaces.

[Configuration of Receptacle Connector]

Next, the configuration of a receptacle connector 50 capable of selectively connecting the above described two kinds of plug connectors 20A and 20B is described.

As shown in FIG. 14 and FIG. 15A to FIG. 15D, the receptacle connector 50 has a box-shaped housing 54 that is formed of an insulating member such as a resin material. An opening 51 into which the plug connectors 20A and 20B can be inserted are formed at the front side of the housing 54. A lever 52a of the locking mechanism portion 52 is disposed on the top of the opening 51, and a lid member 53 is provided at a position that is slightly recessed from the front of the opening 51.

Further, a groove portion 55 into which fits the protrusion portions 25a and 25b of the first plug connector 20A or the protrusion portion 35 of the second plug connector 20B is provided in a lower inner wall on a side opposite to the locking mechanism portion 52 inside the opening 51 of the housing 54. The groove portion 55 is provided for selecting the device to be permitted to connect via the receptacle connector 50. The groove shape (fitting shape) or number of grooves or the like is appropriately set in consideration of the shape of the protrusion portion(s) on the side of the plug connector of the device to be permitted to make a connection.

Figure 15A:
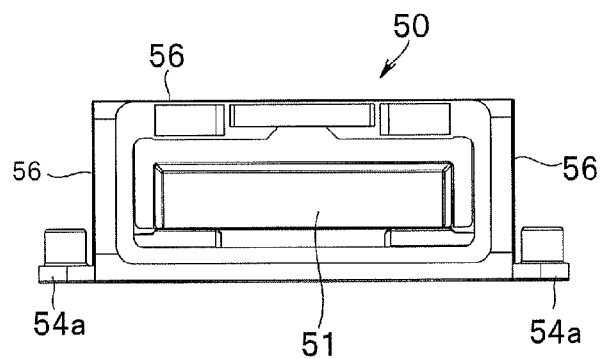
FIG. 15A is a front view of the receptacle connector.
Figure 15B:
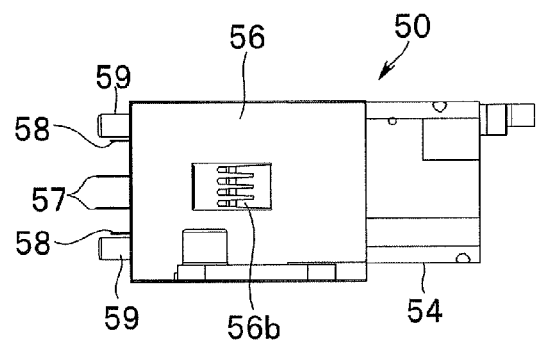
FIG. 15B is a left side view of the receptacle connector.
Figure 15C:
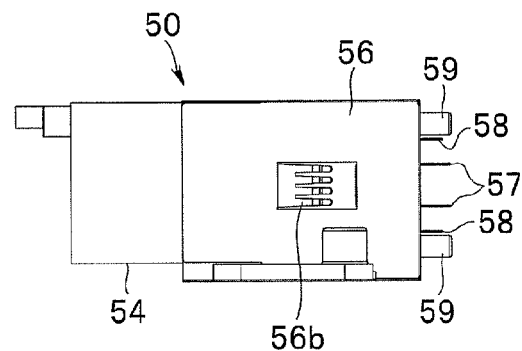
FIG. 15C is a right side view of the receptacle connector.
Figure 15D:
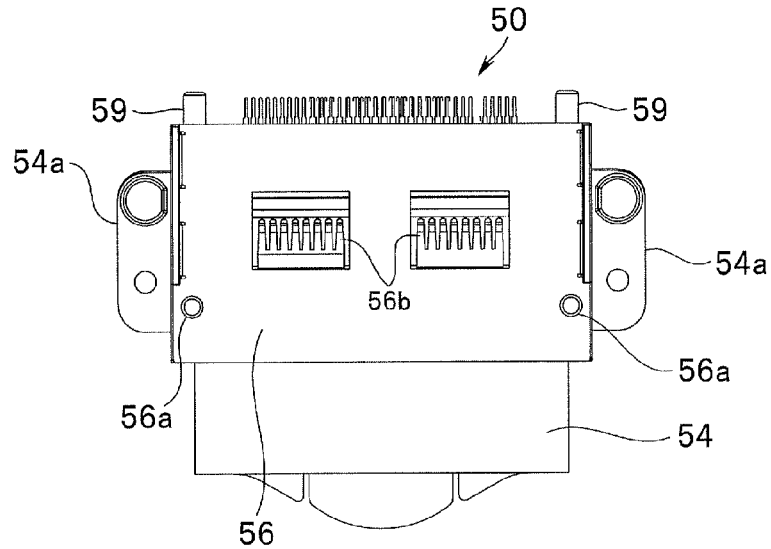
FIG. 15D is a top view of the receptacle connector.

Regarding FIG. 15A to FIG. 15D that illustrate the receptacle connector 50, FIG. 15A is a view that shows the opening 51 side as the front, FIG. 15B is a left side view, FIG. 15C is a right side view, and FIG. 15D is a top view. On both side surfaces at the rear portion of the housing 54 are provided flange portions 54a for attaching and fixing the housing 54 to a device. The side wall surfaces on the top and bottom and left and right of the regions where the flange portions 54a are provided are covered with a shield member 56 for preventing the mixing of noise. The shield member 56 is made from an electrically conductive thin-plate material.

Female screws 56a are formed at both ends on the surface covering the top surface of the housing 54 of the shield member 56. It is possible to directly attach a grounding member to the shield member 56 using the female screws 56a, and the workability of the assembly operations can be improved as the attaching work is performed in the same direction as the direction in which the housing 54 is attached via the flange portions 54a.

The shield member 56 is subjected to stamping at predetermined positions on the top, bottom, left, and right surfaces thereof to form pectinate fingers 56b. The fingers 56b are bent so that the distal-end side thereof extends into the inside of the housing 54, and are configured so as to resiliently contact against the grounding conductive members 30 provided on the top and bottom surfaces of the first plug connector 20A or the grounding conductive members 41 provided on the top, bottom, left, and right surfaces of the second plug connector 20B when the first plug connector 20A or the second connector 20B is inserted and fitted into the receptacle connector 50.

Figure 16:
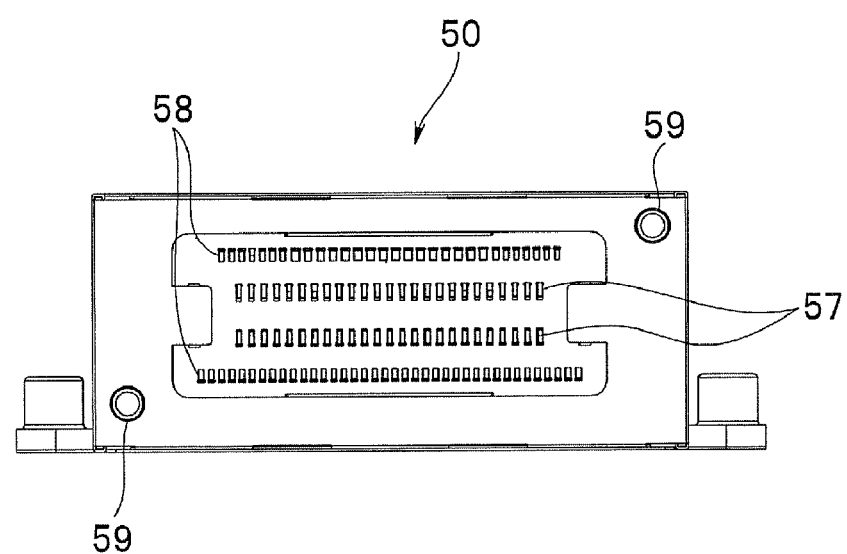
FIG. 16 is a rear view of the receptacle connector.
Figure 17:
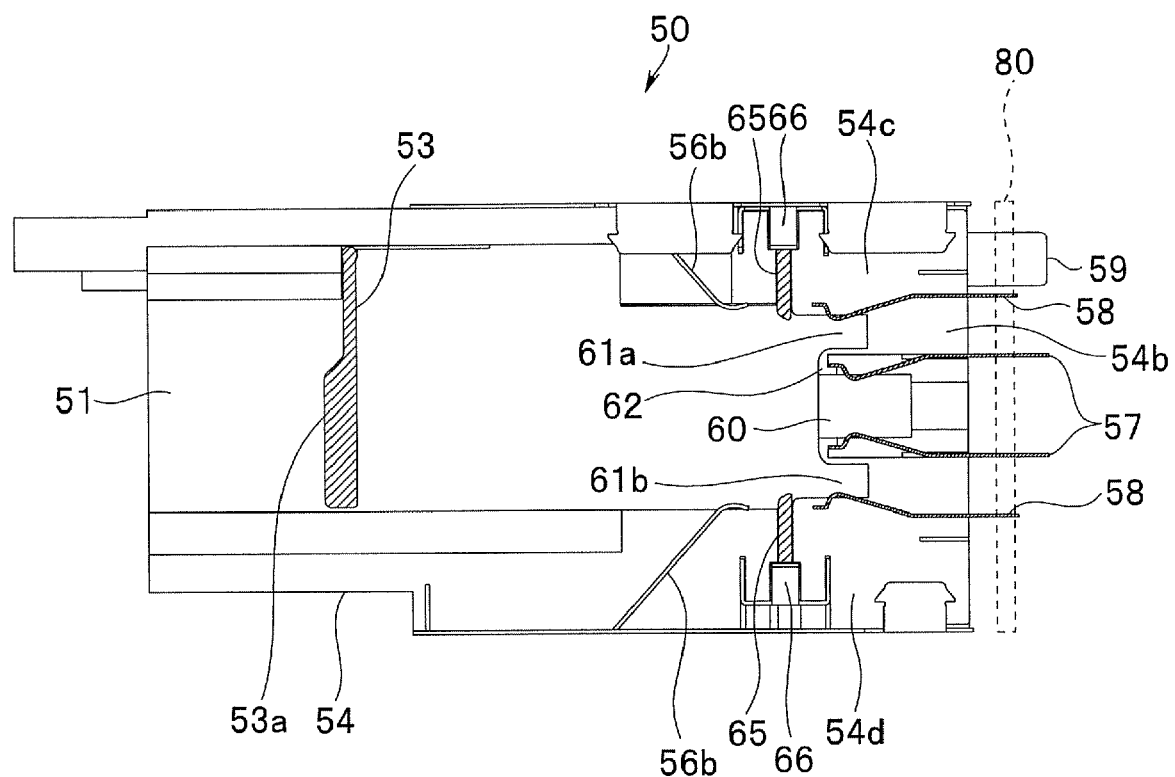
FIG. 17 is a sectional view that shows the configuration of a receiving-side contact of the receptacle connector.

On the rear surface side of the housing 54, a plurality of receiving-side contacts that contact and enter a state of conduction with each of the electrical contacts of the first and second plug connectors 20A and 20B are provided in the housing 54, and the terminals of each receiving-side contact extends rearward from the rear surface of the housing 54. As shown in FIG. 16 and FIG. 17, the receiving-side contacts are arranged in four rows from the top to bottom. The two rows of receiving-side contacts 57, 57 . . . on the inner sides are provided as first receiving-side contacts that contact and enter a state of conduction with the electrical contacts 28, 28 . . . of the first plug connector 20A, and the receiving-side contacts 58, 58 . . . that are disposed above and below the first receiving-side contacts and that contact and enter a state of conduction with the electrical contacts 39, 39 . . . of the second plug connector 20B are provided as second receiving-side contacts.

A substrate 80 as shown by the broken line in FIG. 17 is connected to the first receiving-side contacts 57, 57 . . . and the second receiving-side contacts 58, 58 . . . , and each circuit portion within the relevant device (in the present embodiment, the video processor 3) is connected via the substrate 80. In this case, because there are a large number of terminals, if the protruding length of the terminals of all of the receiving-side contacts is the same, there is a risk that workability will be lost with respect to the soldering work for the terminals or for mounting the substrate 80.

Therefore, as shown in FIG. 17, the amount of protrusion of the terminals is made longer for the first receiving-side contacts 57, 57 . . . than for the second receiving-side contacts 58, 58 . . . that are arranged above and below the first receiving-side contacts 57, 57 . . . . Thus, when performing work to attach the substrate 80, first the receiving-side contacts 57, 57 . . . on the inner sides that have the longer terminals are inserted into holes of the substrate 80, and next the second receiving-side contacts 58, 58 . . . on the outer sides are inserted into holes of the substrate 80. As a result, the work to mount the substrate 80 can be performed reliably and easily. Further, for the soldering work after mounting the substrate 80, by making the length of terminals on the outer sides relatively short, it is possible to improve the workability with respect to soldering the terminals on the inner sides for which the workability is relatively poor. In this connection, a boss 59 that serves as a reference guide when mounting the substrate 80 is vertically arranged on the rear surface side of the housing 54.

The first receiving-side contacts 57, 57 . . . and the second receiving-side contacts 58, 58 . . . are arranged inside the housing 54 as the contact structure shown in FIG. 17. More specifically, in the interior of the opening 51 of the housing 54 are formed a first groove portion 60 into which the protruding portion 29 of the first plug connector 20A can be fitted and a pair of second groove portions 61a and 61b into which the pair of protruding portions 38a and 38b of the second plug connector 20B can be fitted, with the pair of second groove portions 61a and 61b being arranged on the top and bottom so as to enclose the first groove portion 60.

The first groove portion 60 is provided at the center of a protrusion portion 62 that protrudes in an elongated manner in the width direction of the housing 54 from a wall portion 54b that constitutes a rear surface of the inside of the housing 54. The first receiving-side contacts 57, 57 . . . are embedded in two rows on the top and bottom in the protrusion portion 62, and the distal-end portions of the receiving-side contacts 57, 57 . . . are exposed from an opening formed in the inner wall surface at the top and bottom of the first groove portion 60. Thus, when the protruding portion 29 of the first plug connector 20A is fitted into the first groove portion 60, the receiving-side contacts 57, 57 . . . of the receptacle 50 mechanically contact with the electrical contacts 28, 28 . . . of the first plug connector 20A with a predetermined urging force to enable electrical conduction.

Further, the second groove portions 61a and 61b are respectively formed by side surfaces on the top and bottom of the protrusion portion 62, a wall portion 54b constituting the rear surface in the interior of the housing 54, and wall portions 54c and 54d that constitute wall surfaces on the top and bottom of the housing 54. Among the second receiving-side contacts 58, 58 . . . , the distal-end portions of the receiving-side contacts on the upper side are exposed from inner wall surfaces at the top of the groove portion 61a, and the distal-end portions of receiving-side contacts on the bottom side are exposed from inner wall surfaces at the bottom of the groove portion 61b.

Thus, when the pair of protruding portions 38a and 38b of the second plug connector 20B are fitted into the second groove portions 61a and 61b, the receiving-side contacts 58, 58 . . . of the receptacle 50 mechanically contact with the electrical contacts 39, 39 . . . of the second plug connector 20B with a predetermined urging force to enable electrical conduction.

Further, inside the opening 51 of the housing 54 is provided a wiper mechanism that wipes off moisture that adheres to the contact portion of the second plug connector 20B. The wiper mechanism mainly includes wiper members 65 as first wipers that are provided at the front of the first groove portion 60 and the second groove portions 61a and 61b, and a lid member 53 as a second wiper that is provided at the entrance side of the opening 51.

The lid member 53 has a width and height that is capable of blocking the opening 51, and is rotatably supported by the housing 54. The lid member 53 is provided with a step-shaped wiping portion 53a that wipes off moisture that adheres to the contact disposition surfaces 42 by rotating in manner that follows the contact disposition surfaces 42 that are enclosed by the step portion 43 when the second plug connector 20B is inserted. More specifically, in addition to a function of preventing entry of foreign matter from the opening 51 when the receptacle connector 50 is not in use, the lid member 53 also functions as an auxiliary second wiper that wipes off, in a general manner, moisture that adheres to the second plug connector 20B before the second plug connector 20B contacts against the wiper members 65 as first wipers.

Meanwhile, the wiper members 65 provided at the front of the first groove portion 60 and the second groove portions 61a and 61b are provided for wiping off any small quantities of moisture that remain after wiping by the lid member 63. The wiper members 65 function as first wipers that wipe off moisture that attaches to the periphery of electrical contacts, and serve as main elements for preventing electrolytic corrosion of electrical contacts. The wiper members 65 are formed in a plate shape by, for example, integrally molding silicone rubber or the like into a resin element, and are disposed in a condition in which the wiper members 65 are movable back and forth in a substantially orthogonal direction to the insertion direction of the plug connector 20B inside the wall portion 54c and wall portion 54d at the top and bottom of the housing 54, respectively, and are urged towards the outer circumferential surface of the second plug connector 20B by an elastic member 66 composed by a plate spring or the like.

Figure 18:
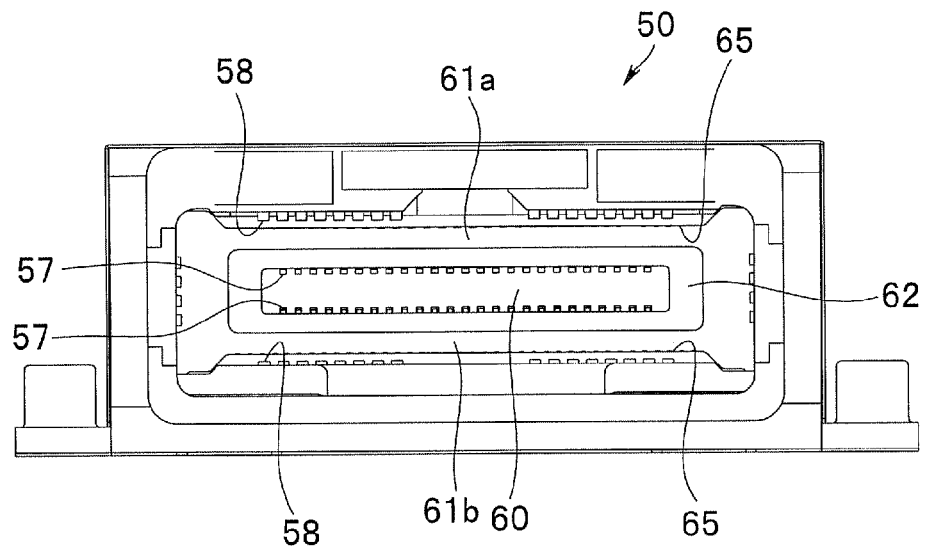
FIG. 18 is an explanatory drawing that illustrates wiper members of the receptacle connector.
Figure 19:
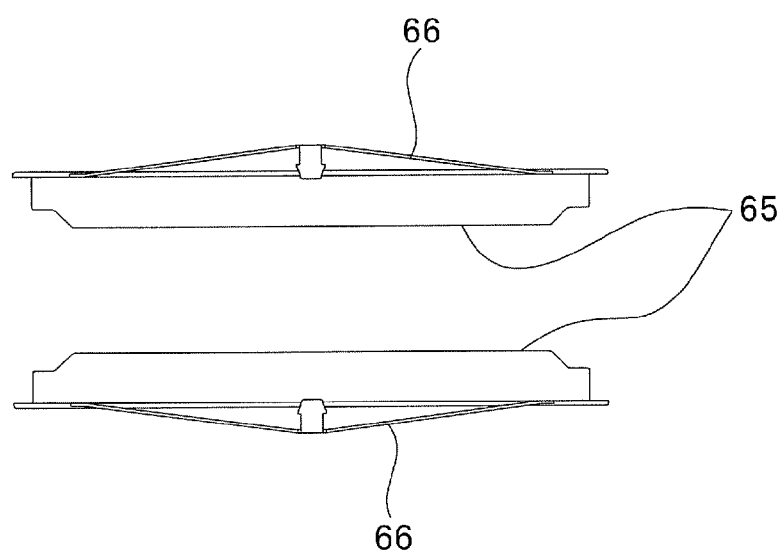
FIG. 19 is an explanatory drawing that illustrates a support structure of the wiper members.

As shown in FIG. 18, when viewed from the opening 51 side of the housing 54, the wiper members 65 are formed in a substantially trapezoidal shape so as to include at least the contact disposition surfaces 42 enclosed by the step portion 43 of the second plug connector 20B as wipeable areas. Further, as shown in FIG. 19, both ends of the wiper members 65 are suspended in a bridge shape by elastic members 66 so that the wiper members 65 are attached in a condition in which the wiper members 65 can move back and forth facing the contact disposition surfaces 42. Thus, when fitting the protruding portions 38a and 38b of the second plug connector 20B into the groove portions 61a and 61b, the distal-end sides of the wiper members 65 intimately contact with the contact disposition surfaces 42 and even if there is only a slight quantity of moisture remaining thereon, the moisture can be effectively wiped off.

In this connection, FIG. 18 also illustrates a state in which the first receiving-side contacts 57, 57 . . . of the first groove portion 60 are arranged so as to surrounded by the end faces of the protrusion portion 62, and it will be understood that the receiving-side contacts 57, 57 . . . are configured such that the contacts cannot be easily touched by a finger or foreign matter. The same applies with respect to the second receiving-side contacts 58, 58 . . . of the second groove portions 61a and 61b that are formed at the top and bottom of the protrusion portion 62.

[Connection Between Receptacle Connector and Plug Connector]

Next, connection between the first and second plug connectors 20A and 20B and the receptacle connector 50 that have the above configurations is described. In the following description, for convenience, it is assumed that connection is made with the "UP" marks 23 and 33 of the plug connectors 20A and 20B on the top side, although the present invention is not limited thereto.

(Connection of First Plug Connector)

Figure 20:
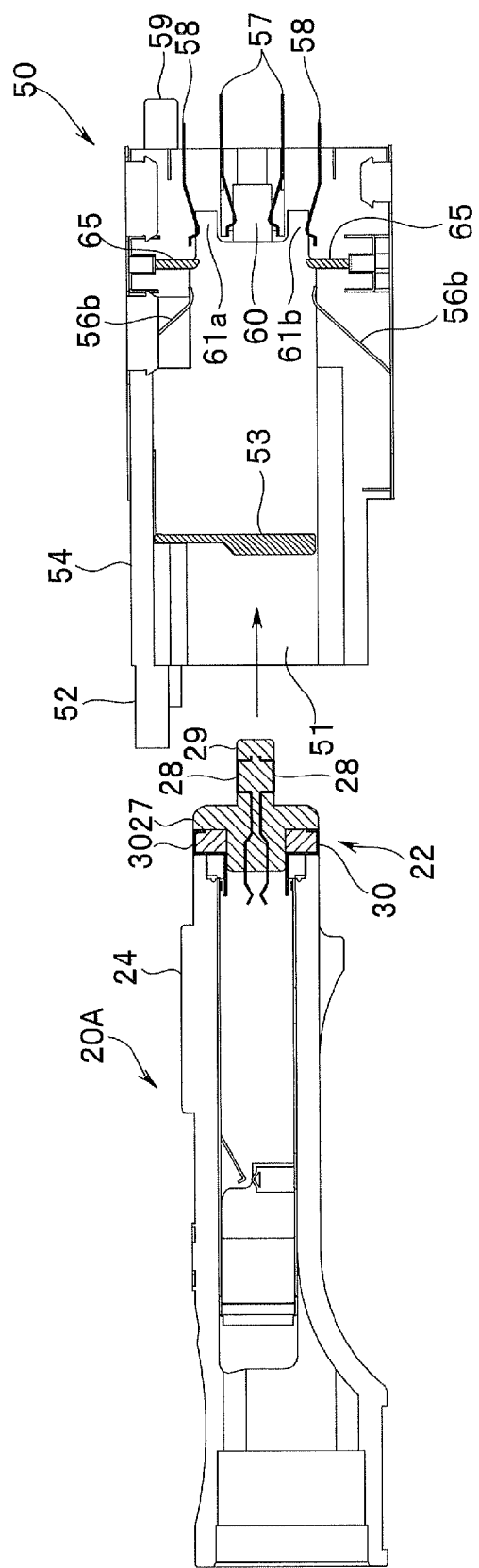
FIG. 20 is an explanatory drawing that illustrates an operation to connect the first plug connector to the receptacle connector.
Figure 21:
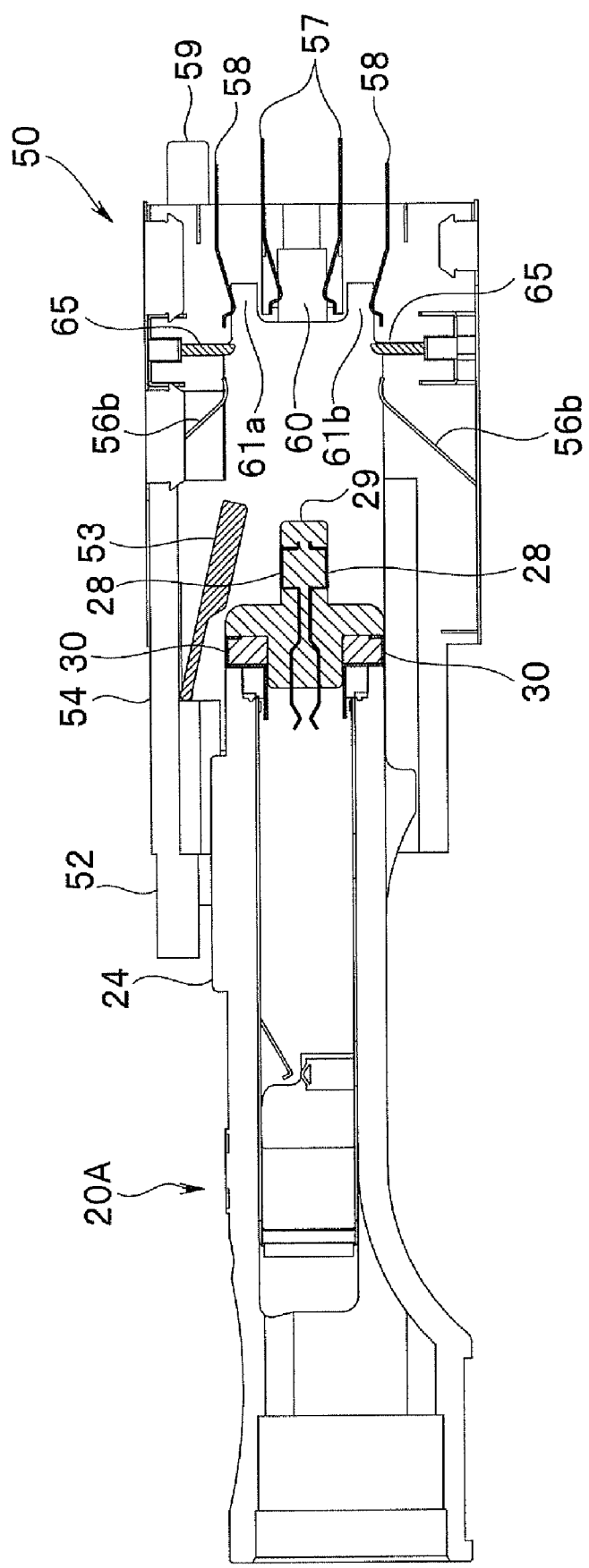
FIG. 21 is an explanatory drawing that illustrates a state in which the first plug connector is inserted partway into the receptacle connector.
Figure 22:
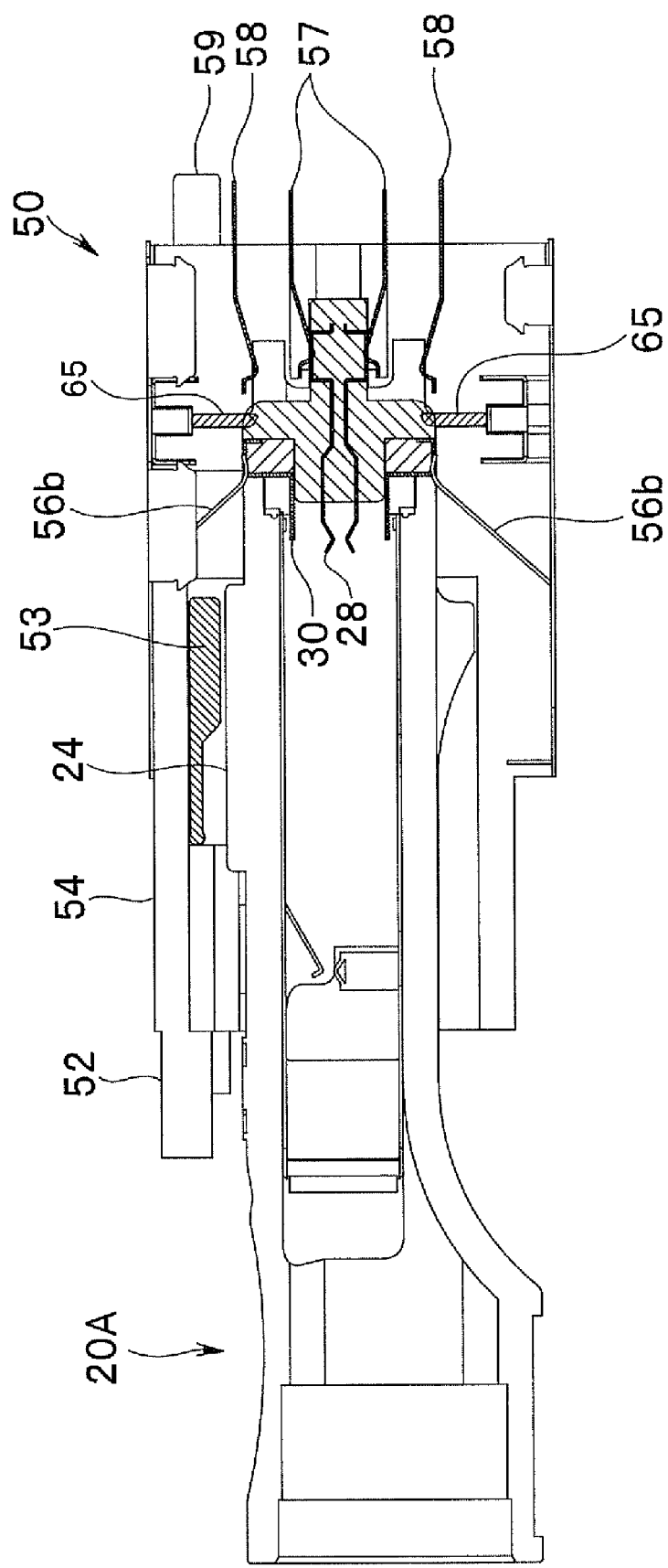
FIG. 22 is an explanatory drawing that illustrates a state in which the first plug connector has been fitted into the receptacle connector.

First, a case in which the first plug connector 20A is connected to the receptacle connector 50 is described using FIG. 20 to FIG. 22.

First, as shown in FIG. 20, the worker grips the first plug connector 20A in a substantially horizontal manner, and brings the first plug connector 20A to the front side of the opening 51 of the receptacle connector 50. Next, as shown in FIG. 21, when the worker inserts the first plug connector 20A into the housing 54 while holding the first plug connector 20A in a substantially horizontal state, the lid member 53 of the receptacle connector 50 contacts against the flange portion 27 of the terminal retaining portion 22 of the first plug connector 20A and the lid member 53 rotates.

Further, as shown in FIG. 22, when the worker continues to insert the first plug connector 20A inside the housing 54, the protruding portion 29 at the tip of the first plug connector 20A is fitted with a predetermined resistance into the groove portion 60 provided in the interior portion of the housing 54. At this time, the protrusion portion 24 on the "UP" mark 23 side of the first plug connector 20A side engages with the locking mechanism portion 52 so that the first plug connector 20A is locked in the receptacle connector 50.

In a state in which the first plug connector 20A has been fitted into the receptacle connector 50, the tips of the fingers 56b on the top and bottom of the shield member 56 provided on the outer circumference of the housing 54 contact against and urge the grounding conductive members 30 provided on the top and bottom surfaces of the flange portion 27 of the first plug connector 20A, and the receiving-side contacts 57, 57 . . . that are exposed inside the groove portion 60 contact against the electrical contacts 28, 28 . . . arranged in the protruding portion 29 and press against the electrical contacts 28, 28 . . . with a predetermined urging force. As a result, a predetermined contact pressure is secured between the electrical contacts 28, 28 . . . of the first plug connector 20A and the receiving-side contacts 57, 57 . . . of the receptacle connector 50 to thus enable reliable electrical conduction.

(Connection of Second Plug Connector)

Figure 23:
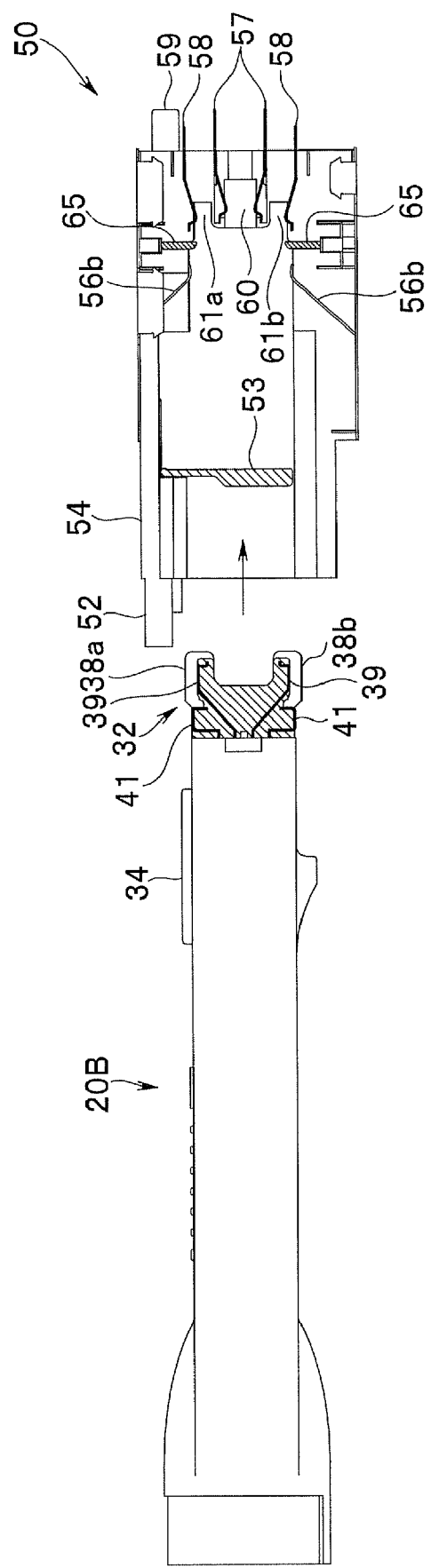
FIG. 23 is an explanatory drawing that illustrates an operation to connect the second plug connector to the receptacle connector.
Figure 24:
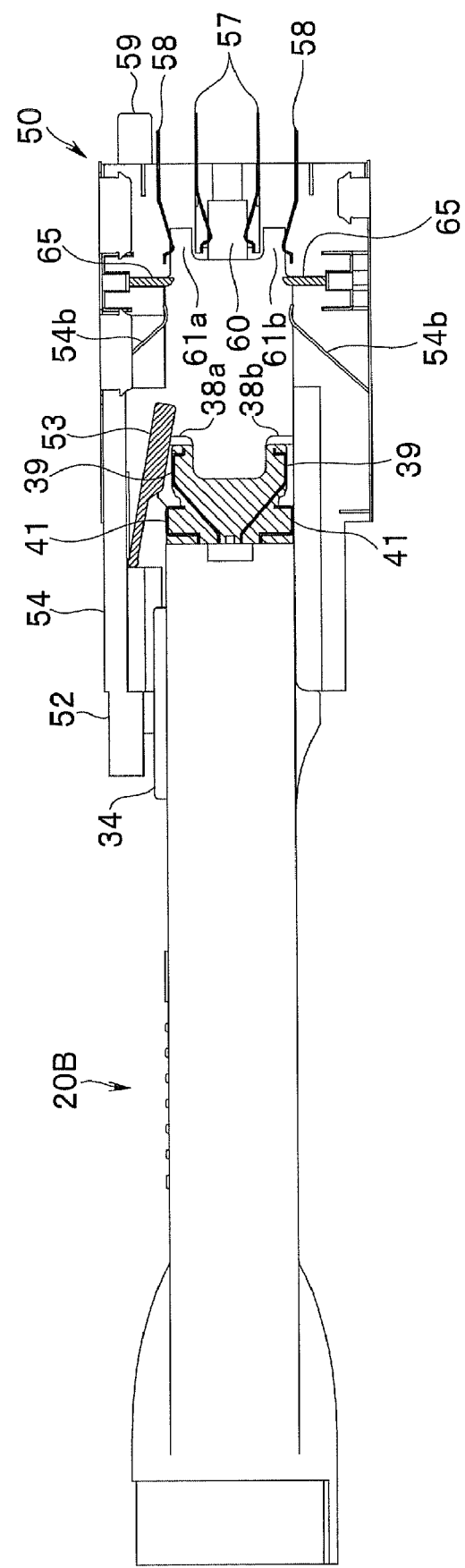
FIG. 24 is an explanatory drawing that illustrates a state in which the second plug connector is inserted partway into the receptacle connector.
Figure 25:
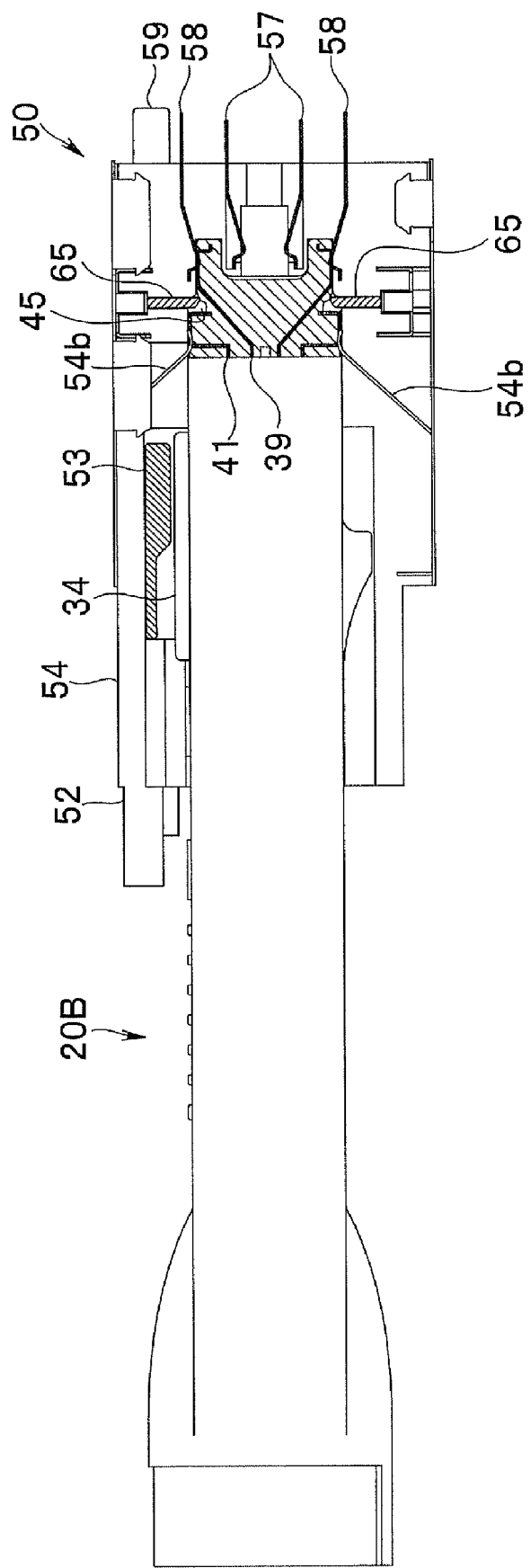
FIG. 25 is an explanatory drawing that illustrates a state in which the second plug connector has been fitted into the receptacle connector.

Next, a case in which the second plug connector 20B is connected to the receptacle connector 50 is described using FIG. 23 to FIG. 25.

As shown in FIG. 23, the worker grips the second plug connector 20B in a substantially horizontal manner, and brings the second plug connector 20B to the front side of the opening 51 of the receptacle connector 50. Next, as shown in FIG. 24, when the worker inserts the second plug connector 20B into the housing 54 while holding the second plug connector 20B in a substantially horizontal state, the lid member 53 of the receptacle connector 50 rotates by following the contact disposition surfaces 42 of the electrical contacts 39 provided in the protruding portion on the upper side among the pair of protruding portions 38a and 38b that are protruded from the terminal retaining portion 32 of the second plug connector 20B, and in a case where moisture adheres to the circumference of the electrical contacts 39, the lid member 53 wipes off that moisture.

Further, when the worker continues to insert the second plug connector 20B inside the housing 54, the distal-end sides of the top and bottom wiper members 65 touch each of the contact disposition surfaces 42 of the pair of protruding portions 38a and 38b and come in intimate contact with the contact disposition surfaces 42. When small amounts of moisture that have not been wiped off completely by the lid member 53 remain on the contact disposition surfaces 42, when the worker continues to move the second plug connector 20B in the insertion direction, the residual moisture is wiped off by the wiper members 65 that intimately contact with the contact disposition surfaces 42. In this case, as shown in FIG. 25, the moisture that is wiped off is accumulated within a groove-shaped concave portion 45 provided on the proximal side of the terminal retaining portion 32, and the protruding portions 38a and 38b of the second plug connector 20B are fitted with a predetermined resistance into second groove portions 61a and 61b provided at the top and bottom of the first groove portion 60. At the same time, the protrusion portion 34 on the "UP" mark 33 side of the second plug connector 20B engages with the locking mechanism portion 52 so that the second plug connector 20B is locked in the receptacle connector 50.

In a state in which the second plug connector 20B has been fitted in the receptacle connector 50, the tips of fingers 56b on the top, bottom, left, and right of the shield member 56 provided on the outer circumference of the housing 54 contact with and urge the grounding conductive members 41 provided on top, bottom, left, and right of the proximal side of the terminal retaining portion 32 of the second plug connector 20B, and the receiving-side contacts 58, 58 . . . that are exposed inside the groove portions 61a and 61b contact with the electrical contacts 39, 39 . . . arranged in the protruding portions 38a and 38b and press against the electrical contacts 39, 39 . . . with a predetermined urging force. As a result, a predetermined contact pressure is secured between the electrical contacts 39, 39 . . . of the second plug connector 20B and the receiving-side contacts 58, 58 . . . of the receptacle connector 50 to thus enable reliable electrical conduction.

According to the present embodiment as described above, two plug connectors 20A and 20B which have a different number of contacts and a different external shape to each other can be selectively connected to a single receptacle connector 50. Moreover, a configuration is adopted such that two kinds of receiving-side contacts that contact with respective first contacts of the two plug connectors 20A and 20B can be mounted using the minimum space within a single receptacle connector 50. It is therefore possible to reduce the mounting space of the receptacle connector to prevent an increase in the size of the apparatus, and also improve the usability.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electrical connector, comprising:
a first plug connector having a first protruding portion and first contacts arranged flat on an outer surface of the first protruding portion;
a second plug connector having a pair of second protruding portions and second contacts respectively arranged flat on outer surfaces of the pair of second protruding portions; and
a receptacle connector that includes:
an opening into which the first plug connector and the second plug connector can be selectively inserted,
a first groove portion that is provided inside the opening, and into which the first protruding portion of the first plug connector can fit,
first receiving-side contacts that are arranged flat inside the first groove portion so as to electrically conduct with the first contacts in a state in which the first protruding portion has been fitted therein,
a pair of second groove portions that are provided so as to surround the first groove portion, and into which the pair of second protruding portions can fit, and
second receiving-side contacts that are arranged flat inside the pair of second groove portions, respectively, so as to electrically conduct with the second contacts in a state in which the pair of second protruding portions have been fitted therein.

2. The electrical connector according to claim 1, wherein a concave portion that is larger than the first groove portion of the receptacle connector is formed between the pair of second protruding portions in the second plug connector.

3. The electrical connector according to claim 1, wherein, in the receptacle connector, an external wall surface of a housing in which the first receiving-side contacts and the second receiving-side contacts are internally arranged is covered with a conductive shield member that resiliently contacts with a grounding conductive member provided in the first plug connector or a grounding conductive member provided in the second connector.

4. The electrical connector according to claim 3, wherein pectinate fingers that resiliently contact with the conductive member of the first plug connector or the conductive member of the second connector are integrally formed in the shield member.

5. The electrical connector according to claim 1, wherein, in the receptacle connector, lengths of terminals protruding from a housing in which the first receiving-side contacts and the second receiving-side contacts are internally arranged are provided such that terminals of the first receiving-side contacts are longer than terminals of the second receiving-side contacts.

6. An electrical connector according to claim 1, wherein the first protruding portion protrudes from a front end of an exterior case of the first plug connector and the first contacts comprise a plurality of electrical contacts, and the pair of second protruding portions protrude from a front end of an exterior case of the second plug connector and the second contacts comprise a plurality of electrical contacts, the pair of second protruding portions being spaced at an interval that is greater than a thickness of the first protruding portion.

7. An electrical connector, comprising;
a first plug connector having a first protruding portion and first contacts arranged flat on an outer surface of the first protruding portion;
a second plug connector having a pair of second protruding portions and second contacts respectively arranged flat on outer surfaces of the pair of second protruding portion, the pair of second protruding portions being spaced at an interval that is greater than a thickness of the first protruding portion; and
a receptacle connector that is capable of selectively connecting the first plug connector and the second plug connector.

8. An electrical connector, comprising:
a first plug connector having a first protruding portion and first contacts arranged flat on an outer surface of the first protruding portion;
a second plug connector having a pair of second protruding portions and second contacts respectively arranged flat on outer surfaces of the pair of second protruding portions, the pair of second protruding portions being spaced at an interval that is greater than a thickness of the first protruding portion of the first plug connector; and
a receptacle connector in which first receiving-side contacts capable of electrically conducting with the first contacts of the first plug connector are arranged flat inside a first groove portion into which the first protruding portion of the first plug connector can fit, and in which second receiving-side contacts capable of electrically conducting with the second contacts of the second plug connector are arranged flat inside a pair of second groove portions into which the pair of second protruding portions of the second plug connector that are provided so as to surround the first groove portion can fit.

* * * * *